United States Patent [19]
Stern et al.

[11] Patent Number: 5,422,103
[45] Date of Patent: * Jun. 6, 1995

[54] HIGH DOSAGE TOPICAL FORMS OF COLLAGENASE

[75] Inventors: Harold Stern, Baldwin Harbor; David Yee, Oceanside, both of N.Y.

[73] Assignee: Advance Biofactures of Curacao, N.V., Curacao, Netherlands Antilles

[*] Notice: The portion of the term of this patent subsequent to Feb. 28, 2012 has been disclaimed.

[21] Appl. No.: 157,935

[22] Filed: Nov. 24, 1993

Related U.S. Application Data

[63] Continuation-in-part of Ser. No. 795,915, Nov. 20, 1991, abandoned, and Ser. No. 963,995, Oct. 29, 1992, Pat. No. 5,393,792.

[51] Int. Cl.$^6$ ............ A61K 31/74; A61K 37/54; A61L 15/16; A61L 9/50
[52] U.S. Cl. ............ 424/78.06; 424/444; 424/499; 424/94.67; 514/59; 514/777
[58] Field of Search ............ 424/78.06, 444, 499, 424/94.67; 514/59, 777; 435/212, 219, 220; 530/813, 825; 536/112

[56] References Cited

PUBLICATIONS

Harper E., "Collagenases", *Ann Rev Biochem*, 1980, 49:1063–78.

*Primary Examiner*—Thurman K. Page
*Assistant Examiner*—Carlos Azpuru
*Attorney, Agent, or Firm*—Roland Plottel

[57] ABSTRACT

This invention provides pharmaceutical compositions for topical application containing high concentrations of the enzyme collagenase in non-aqueous excipients. The invention also provides a particular excipient, dextran, which is especially useful for admixture with collagenase and which can also be used to advantage with othr pharmaceutically active materials.

20 Claims, 3 Drawing Sheets

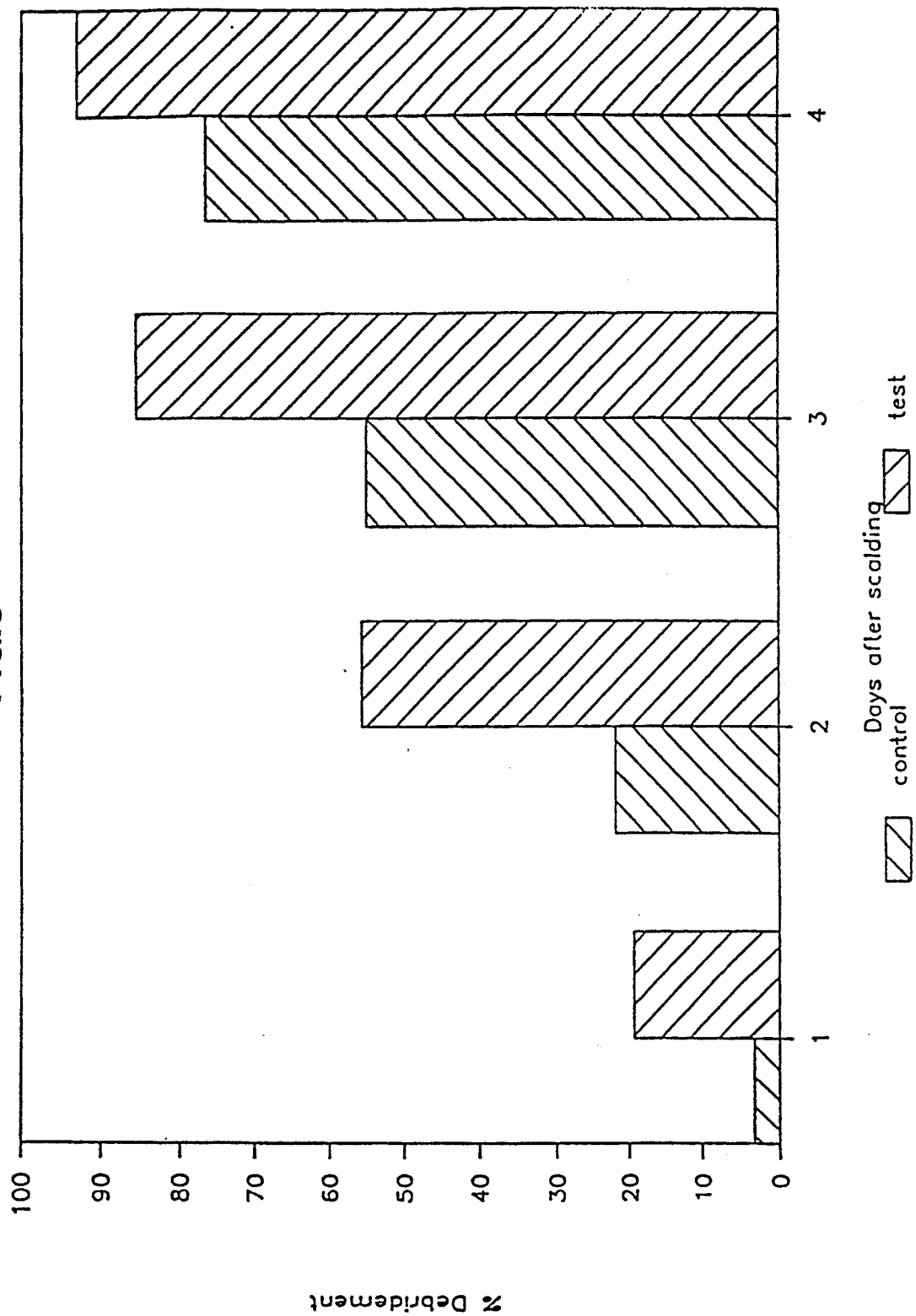

HIGH DOSAGE TOPICAL FORMS OF COLLAGENASE

This application is a continuation-in-part of U.S. Ser. No. 07/795,915, filed Nov. 20, 1991, now abandoned; and is a continuation-in-part of U.S. Ser. No. 07/963,995, filed Oct. 29, 1992, now U.S. Pat. No. 5,393,792.

BACKGROUND OF THE INVENTION

Collagenase ointment has been available in the United States as Collagenase Santyl ® Ointment (Advance Biofactures Corp., Lynbrook, N.Y. 11563) for 27 years. It has been used on millions of patients. The concentration of collagenase in Santyl ® Ointment has been no greater than 300 ABC units per gram of ointment. Collagenase ointment has also been available in other countries. It is useful for the debridement of burns and of dermal ulcers, particularly bed sores (decubitus ulcers). The debridement of these lesions is necessary to remove dead and dying tissue that is typically a source of microbial infection. In addition, healing does not take place until this necrotic material is removed. Speed of debridement is thus a therapeutic desideratum.

Collagenase ointment has not been so widely accepted by the burn centers in the treatment of third degree burns as perhaps its efficacy deserves. This lack of acceptance is largely due to the perception that third degree burns in particular require a more rapid debridement than the collagenase ointment can provide. A more rapid debridement of severe burns without the necessity for anesthesia or a surgical operation would constitute a therapeutic advancement.

A more rapid debridement would also be useful in the treatment of dermal ulcers since it wold provide a superior cost/benefit profile.

Dextrans are polysaccharides produced by certain bacteria (e.g. *Leuconostoc mesenteroides*) and consist of chains of $\alpha$-D-glucopyranosyl residues linked predominantly by $\alpha$-(1→6)-linkages, with a small fraction of $\alpha$-(1→3)-linkages which give rise to chain branching. Dextrans are available in various molecular-weight fractions. Dextran fractions with weight average molecular weights of 40,000, 70,000 and 75,000 daltons have found therapeutic uses as plasma volume expanders. The 40,000-dalton fraction is also used as a blood flow adjuvant. [Ref. Merck Index, Tenth Edition, #2911] In addition, dextran is used in lubricant eye drops and hysteroscopy fluids. [ref. PDR, 45th edition, 1991]

Dextrans are commercially available as a fine white powder that is approved for pharmacological use. The powder absorbs water readily and hence is useful as a drying agent for wounds, and is completely soluble in sufficient amounts of water.

Pharmacologically active ingredients such as enzymes, antibiotics, antifungals, anti-inflammatories, antipyritics, etc. are usually diluted with an excipient for topical use as creams, ointments, lotions, solutions, etc. Many such excipients decrease the shelf life of drug substances.

SUMMARY OF THE INVENTION

In accordance with one aspect of this invention, a pharmaceutical composition is prepared by intimately admixing a dry powdered drug substance suited for topical application, with dry powdered dextran. By drug substance or pharmaceutical is meant a material that is pharmaceutically active or that becomes active upon admixture with water.

A preferred embodiment is a dry powdered intimate physical admixture of dextran and collagenase. The enzyme collagenase is derived from fermentation by *Clostridium histolyticum*, and is purified by a chromatographic technique. It possesses the unique ability to digest native and denatured collagen in necrotic tissue. While as little as 100 or even fewer ABC units of collagenase per gram of admixture can be expected to have some efficacy, ordinarily one will use up to 250 or up to at least 500 units. Advantageously, one gram of the admixture contains from 500 to 5,000 ABC units of collagenase; and, as will be explained below, an especially advantageous mixture contains in excess of 2,500 up to 10,000 or more ABC units of collagenase per gram of dextran. It is useful for debridement of burns and of decubitus ulcers, generally known as bed sores. The mixture can be shaken or sprayed onto the burn or ulcer, and a homogeneous mixture of the dextran and collagenase will thus reach the affected site. The fluids available from the wound will dissolve the dextran and make the active enzyme available where it is needed.

This invention further provides pharmaceutical compositions wherein dextran or other non-aqueous excipient is mixed with the enzyme collagenase at a collagenase concentration much greater than has heretofore been used in practice, and higher than heretofore mentioned in the literature to our knowledge. These compositions, when used topically to treat burns, ulcers and other wounds, provide rapid debridement of dead and dying tissue without causing undesirable side effects.

The pharmaceutical compositions of this aspect of the invention contain at least about 1,500 ABC units collagenase per gram of excipient, and preferably range from greater than 2,500 up to 10,000 or more units per gram of excipient. For many applications the concentration will exceed 5,000 units/gram of excipient, e.g., 8,000 units/gram of excipient. In general, within these ranges one should use higher concentrations in powdered or liquid compositions than in ointments, because more of the latter can be applied to and maintained on the area to be treated. Preferred ranges for ointments are about 1,500 to about 5,000 and for powders or liquids are about 2,500 to about 10,000 ABC units collagenase per gram of excipient.

These pharmaceutical compositions are prepared by intimately admixing a sterilized collagenase powder with a non-aqueous solid or liquid excipient. Excipients that can be used include (but are not limited to) dextran, white petrolatum USP, isopropyl myristate NF, and lactose NF. While lactose and other excipients containing as little as about 100 ABC units of collagenase per gram generally have some effect, lactose and other excipients containing from about 1,500 to about 10,000 or more ABC units collagenase per gram are the preferred high-dosage embodiments of the invention. In addition, an antibiotic or antiseptic powder such as Polysporin ® antibiotic, gentamicin, and/or silver sulfadiazine may be added, or may constitute the excipient itself.

By non-aqueous excipient is meant a liquid or solid material that is inert towards, i.e., does not significantly affect adversely the physiological activity of, the collagenase, and that is substantially free from water. Water is an undesired constituent. The water or other aqueous solutions of collagenase taught in the literature, if prepared in advance for use, would generally have a safe shelf life at room temperature of not over two weeks.

DETAILED DESCRIPTION

The potency assay of collagenase is based on the digestion of undenatured collagen (from bovine tendon) at ph 7.2 And 37° C. for 20–24 hours. The number of peptide bonds cleaved are measured by reaction with ninhydrin. Amino groups released by a trypsin digestion control are subtracted. One net ABC unit of collagenase will solubilize ninhydrin reactive material equivalent to 1.09 nanomoles of leucine per minute.

Sterilized collagenase powder is available having a minimum assay of 50 ABC units per mg. The assay may range considerably above that from batch to batch, but is taken into account in determining the weight of powder to admix with excipient to give the desired number of collagenase units per gram of excipient.

Dextrans are useful for the delivery of desired amounts of medication to topical wounds, burns, infections, inflammations, lacerations, ulcers. Included in such medications are collagenase and other enzymes, antibiotics, anesthetics, antifungals, anti-inflammatory agents (steroidal and non-steroidal).

Since the affected area is not touched, the application of the dry powdered mixture of dextran and medication can be less painful than would be the case if the medication were applied as a cream, gel, lotion, ointment, etc. In addition, no cream, gel, lotion, or ointment needs to be removed between dressings: the dextran formulation is soluble, so only gentle lavage with an appropriate liquid, such as sterile water or normal saline, is needed to cleanse the area.

Dry powdered dextrans provide the following further advantages for use in admixture with dry powdered pharmaceuticals:

1. They readily dissolve in the fluids available at a wound site.
2. Their dissolution provides an in situ release of the active ingredient.
3. All of the active ingredient is available at the wound site, as opposed to an ointment, wherein some of the active ingredient may remain trapped in the ointment matrix.

There are also economic advantages to using dextrans as described herein since the mixing and filling of dry ingredients is less costly than the mixing of ointments, creams, and lotions and their filling into tubes and/or glass jars.

Thus dextrans of various molecular weights, fine dry powders that have no intrinsic therapeutic activity and that are well tolerated by man and animals, can safely and advantageously be used as carriers for dry pharmaceuticals when used topically.

Whether application is made by dusting or spraying, a homogeneous dry powdered mixture of the dextran and active ingredient will reach the affected site, and the aqueous fluids available from the wound will dissolve the dextran and make the active ingredient available where it is needed.

Dry powdered intimate admixtures of dextran and one or more topical pharmaceuticals include, by way of example, the following (the percentages are by weight).

A. Dextran with ½–20% collagenase as a debriding agent.

B. Dextran with other enzymes recognized for their therapeutic activity when used topically.

C. Dextran with 0.1% gentamicin as an antibiotic.

D. Dextran with other antibiotics; e.g., neosporin, silver sulfadiazine, chloramphenicol, and other antibiotics deemed safe and effective when used topically.

E. Dextran with ½–20% benzocaine as an anesthetic.

F. Dextran with other topical anesthetics, whether natural or synthetic; e.g. lidocaine, etc.

G. Dextran with 1% clotrimazole as an antifungal agent.

H. Dextran with other topical antifungal agents, e.g. nystatin, ketoconazole.

I. Dextran with 0.01–2½% hydrocortisone as an anti-inflammatory agent.

J. Dextran with other steroidal or nonsteroidal antiinflammatory drugs, e.g. halcinonide, triamcinolone acetonide, that can be used topically.

K. Dextran with other therapeutic agents that are deemed safe and effective when used topically.

While ranges of weight percent are given, one skilled in the pharmaceutical arts will make the choice based on activity of the drug and appropriate concentrations for the intended use. More than one concentration of a particular drug may be made available to the physician. In general, for most pharmaceuticals, the concentration will be within the broad range of about 0.01 to 30 weight percent pharmaceutical in the mixture.

Dextrans used will ordinarily be in the range of about 20,000 to 100,000 daltons molecular weight. The intended use may affect the choice, the higher molecular weights giving a more viscous drug-containing liquid when the powder absorbs exudate from the wound. Powdered dextrans can be employed that have molecular weights down to 1,000 daltons or even lower, up to 500,000 or even 1,000,000 daltons or more. Dextrans from very low to very high molecular weights, being polar, are water-soluble. Dextrans that have been subjected to cross-linking rendering them water-insoluble cannot provide the advantages of our invention.

In accordance with this invention, the dextran and the collagenase or other pharmaceutical are in simple physical admixture, not molecularly bound to each other by an added chemical binding or linking agent. Thus, the invention provides a pharmaceutical composition consisting essentially of dextran and a pharmaceutical suited for topical application in dry powdered intimate physical admixture.

Dextrans and most other dry excipients are available commercially as fine dry powders, as are purified collagenase and most other pharmaceuticals. The mixing of dry powders is within the skill of the art, and various kinds of apparatus can be obtained from commercial suppliers. Taking dextran as an example, it is best to mix and package in a controlled atmosphere of low or zero humidity. For many drugs subject to easy oxidation, an inert atmosphere, e.g. nitrogen or helium, can be used.

Rather than mixing dry powders, it is possible to dissolve dextran or other soluble excipient and the desired pharmaceutical(s) in a solvent, usually water with or without another water soluble solvent such as a lower alcohol, and either precipitate the solutes as by chilling or adding a non-solvent followed by drying, or spray-dry the solution, or lyophilize the solution, to obtain the dry powdered mixture of pharmaceutical and excipient. Drying of a precipitate followed by grinding, if necessary, should be carried out at near room temperature or lower in a selected atmosphere as described above; likewise spray-drying, which can also advantageously be conducted in vacuo. All such operations are within the skill of the art.

The particle size of final product is not critical, so long as it dusts or flows easily.

Since dextrans and a number of other powdered excipients absorb moisture easily, and many drug substances are adversely affected by water, our dry powder pharmaceutical compositions should be packaged so as to prevent moisture from entering: therefore, the material from which the package is constructed should be a vapor barrier, and replaceable closures should insure a tight seal.

Packages may take on a number of forms, selected and designed for different needs:

1. Shaker containers, whereby the mixture can be dusted over open surface areas.
2. Aerosol containers (atomizers), whereby the mixture can be sprayed onto or into an affected area by gentle gas or air pulses.
3. Single unit envelopes, which may contain, say, from ½ to 30 grams of the mixture as a single unit dose. Shaker and/or aerosol containers can be fitted with volume controls so that a predetermined quantity (single unit dose) of the powdered mixture is released.

The preparation of ointments by various procedures is within the skill of the art, and various kinds of apparatus can be obtains from commercial suppliers. The high-dosage collagenase ointments of this invention can be packaged in glass jars, squeezable tubes, or in sealed single unit dose envelopes.

The admixture of finely divided solids with liquids is likewise within the skill of the art, as by using high-speed bladed stirrers or other commercially available apparatus. Liquid compositions of this invention can be packaged in bottles, jars, single unit dose envelopes, or preferably aerosol containers which should be well shaken before use to spray onto or into the area to be treated.

It may be desirable to include in our pharmaceutical compositions one or more other medicaments. Often an antibiotic or antiseptic is added for general prophylaxis against infection and/or to fight infection. Other useful additions are anti-inflammatory agents and local anesthetics or analgesics.

For the convenience of the physician, nurse, or other user, a pharmaceutical kit may be sold containing a shaker, spray can, tube or other package containing a pharmaceutical composition of this invention together with a separate shaker or spray can or other package containing an antibiotic in any conventional form. Rather than or in addition to the antibiotic, one can use in a separate package in the kit any medicament intended to reduce infection or to alleviate pain or to induce general healing.

With respect to our high-dosage collagenase compositions, in addition to the non-aqueous excipients mentioned above, further examples of those that may be used are powdered cornstarch, talc. A further example of ointment base is lanolin (caution: allergenic to a small percentage of the population). Suitable liquid excipients are mineral oil, glycerol. Any material proposed for use as an excipient must first be tested in the intended formulation to determine that it is indeed substantially inert towards the collagenase over a considerable length of time, i.e., the desired assured shelf life.

BRIEF DESCRIPTION OF THE DRAWINGS

FIG. 3 shows percentage debridement as a function of time, as determined in Experiment Number 3 below, using two different concentrations of collagenase in lactose NF, one five times greater than the other.

EXAMPLES OF HIGH-DOSAGE COLLAGENASE

Figure 1:
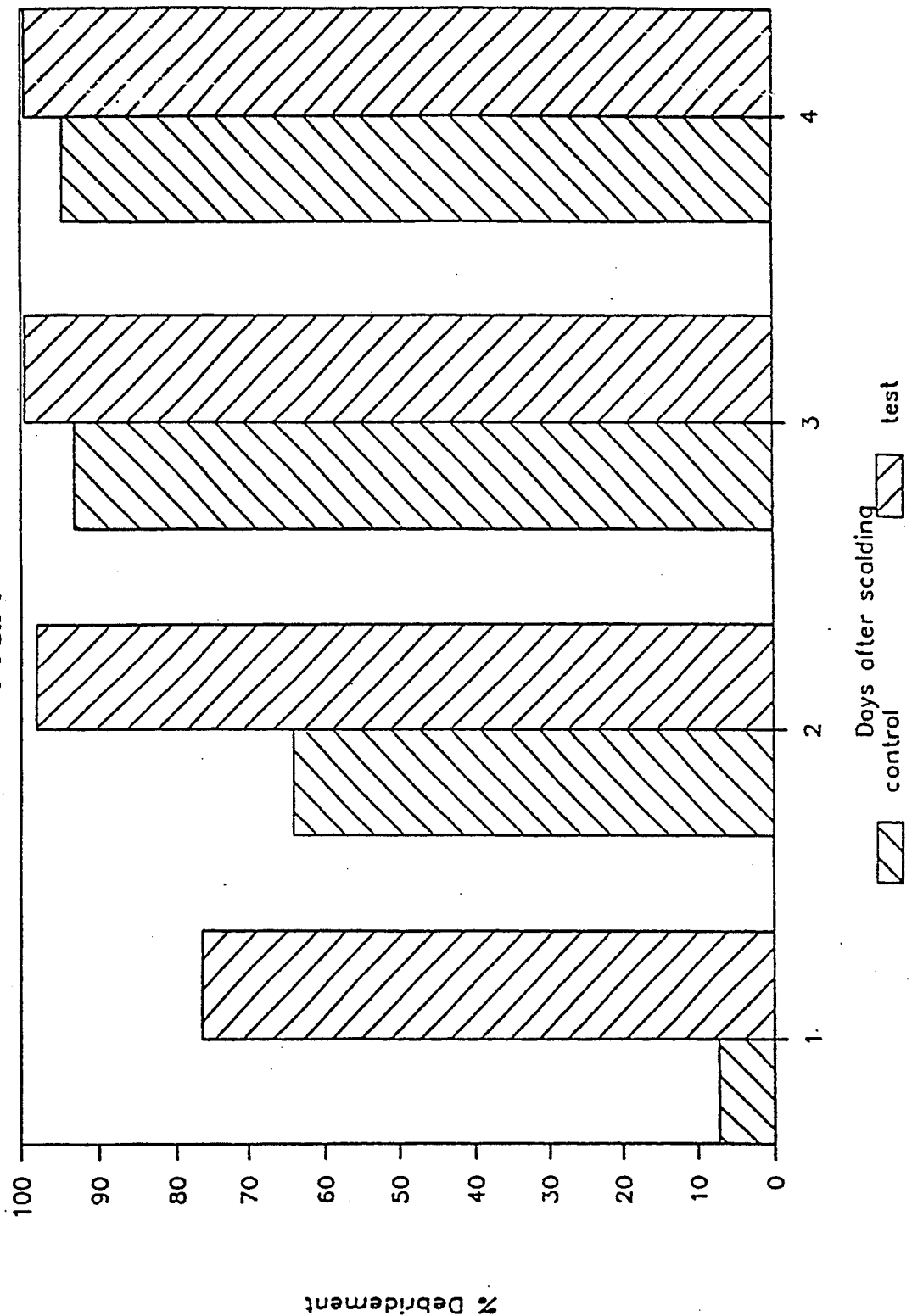
FIG. 1 shows percentage debridement as a function of time, as determined in Experiment Number 1 below, using two different concentrations of collagenase in Polysporin ®, one ten times greater than the other.
Figure 2:
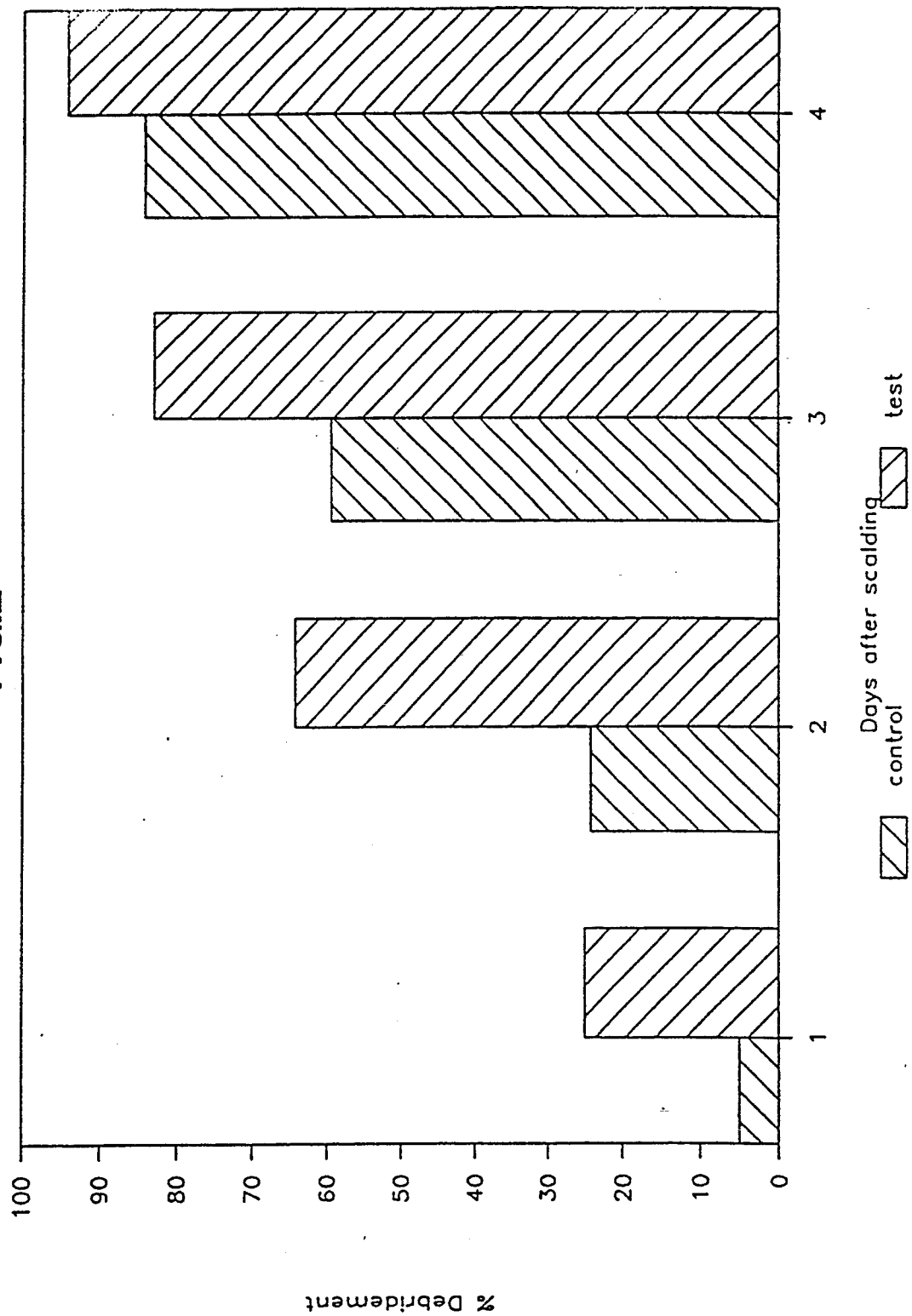
FIG. 2 shows percentage debridement as a function of time, as determined in Experiment Number 2 below, using two different concentrations of collagenase in petrolatum, one ten times greater than the other.

Sterile collagenase powder is available from Advance Biofactures Corporation of Lynbrook, N.Y. 11563.

White petrolatum USP is commercially available from Witco Chemical.

Polysporin ® is commercially available from Burroughs Wellcome.

Lactose NF is commercially available from a number of sources, e.g. DMV Campina, Inc. Lactose is a sugar obtained from milk. It is anhydrous or contains one molecule of water of hydration. Either form can be used as excipient in this invention.

A number of experiments were carried out to compare the debriding effect of a high-dosage pharmaceutical preparation with a normal dose preparation. In each experiment a number of guinea pigs were anesthetized and were given bilateral third degree burns by being scalded for 20 seconds with a 100-ml beaker containing boiling water. This method produces a well-defined burn and burn eschar of a reproducible size. Some of the burns were treated with the standard amount of collagenase. The other burns were treated with up to ten times the standard amount. All burns were treated with antibiotic. The percentage debridement was assessed by visual inspection and by serial photographic evidence.

The following examples illustrate the difference between standard dose preparations and high-dosage preparations.

Experiment Number 1

Eight guinea pigs were given bilateral third degree burns. Seven of the burns were controls and were treated daily by sprinkling approximately 1 g of Polysporin ® which contained 800 ABC units of collagenase powder. The lesion was then covered with a 3×3-inch sterile gauze pad containing a thin layer of sterile petrolatum. This procedure was repeated for 4 days. The test sides were treated in an identical manner, except that each gram of Polysporin ® contained 8,000 ABC units of collagenase powder. (The presence of a Polysporin ®-resistant *Proteus mirabilis* infection necessitated the use of gentamicin powder, which was sprinkled on the wound after treatment with collagenase/Polysporin ® but before covering with the gauze pad. Sides 61L, 61R, 62L, 62R, 13L, 63R, 64L, and 64R were treated with gentamicin on the second, third, and fourth days subsequent to burning.)

The results of this experiment are presented in Table 1 and Chart 1. Note that the average percentage debridement with 8,000 ABC units is significantly better (at the 99% degree of confidence, based on the Wilcoxon test) than the debridement seen with 800 ABC units for all four days.

Experiment Number 2

Eight guinea pigs were given bilateral third degree burns. Half of the burns were controls and were treated daily by applying a sterile gauze pad containing about 3 g of an ointment of white petrolatum USP containing 270 ABC units of collagenase per gram of petrolatum. This procedure was repeated for 4 days. The test sides were treated in an identical manner, except that the petrolatum used contained 2,700 ABC units of collagenase powder per gram of petrolatum. Gentamicin powder was sprinkled onto the burns of animals 80, 81, 82, and 83 before the collagenase/petrolatum ointment was applied. Similarly, silver sulfadiazine powder was used on animals 86, 87, 88, and 89.

The results of this experiment ar presented in Table 2 and Chart 2. Note again that the high-dosage treatment debrided significantly faster than the standard-dose treatment.

Experiment Number 3

Seven guinea pigs were given bilateral third degree burns. Half of the burns were controls and were treated daily by sprinkling on the wound silver sulfadiazine followed by approximately 1 g of lactose NF that contained 800 ABC units of collagenase powder. The burn was then covered with a 3×3-inch sterile gauze pad containing a thin layer of sterile petrolatum. This procedure was repeated for 4 days. The test sides were treated in an identical manner, except that each gram of lactose NF contained 4,000 ABC units of collagenase powder.

The results of this experiment are presented in Table 3 and Chart 3. Note again that the high-dosage treatment debrided significantly faster than the standard dose treatment.

Experiment Number 4

The objective was to evaluate the efficacy and safety of collagenase in powdered lactose monohydrate NF in various dosages with concomitant application of silver sulfadiazine cream. Five (5) white recently weaned female cross-bred swine weighing between 36.25 and 39.75 pounds at study onset were the test animals. In order to accommodate five treatment groups, 16 full thickness dermal burns were inducted on anesthetized pigs. The wounds were created in pairs at least three centimeters apart and each pair was evaluated by the investigator as a single burn field. Third degree or full thickness burns were created with a brass rod, one inch in diameter heated in 100 degree centigrade water, dried, and placed on the skin for sixty seconds. Treatment assignment was scrambled to account for regional healing differences. Due to limitations of the size of the animal, treatment with 3,750 ABC units collagenase per gram and with Petroleum Jelly (petrolatum) control had half the burn sample size as the other dosage groups.

| | | |
|---|---|---|
| 1) Collagenase/Lactose | 750 ABC u/g | 10 Burn Fields |
| 2) Collagenase/Lactose | 3,750 ABC u/g | 5 Burn Fields |
| 3) Collagenase/Lactose | 7,500 ABC u/g | 10 Burn Fields |
| 4) Collagenase Ointment (Santyl ®) | 250 ABC u/g | 10 Burn Fields |
| 5) Petroleum Jelly (Control) | | 5 Burn Fields |

Administration was topical. Wound eschar was crosshatched with a scalpel. Collagenase in lactose monohydrate NF was dusted directly on the burn wound following induction. A thin layer of silver sulfadiazine cream was applied onto a petroleum jelly layered gauze and secured to the wound. Wounds treated with Collagenase Santyl ® Ointment had the ointment applied to the burn surface and covered with gauze layered with silver sulfadiazine. Wounds assigned to the control group were secured with petroleum jelly layered gauze covered with silver sulfadiazine.

Test articles were applied once daily during dressing changes. Test articles were discontinued after the investigator considered the wound bed clean as evidenced by absence of retained necrotic debris. The study was finished after all treated areas were considered to be 100% re-epithelialized.

Treatment with the various test articles resulted in a total daily dosage of approximately 10,092 ABC units collagenase per animal.

DEBRIDEMENT

Debridement was estimated daily by the investigator during the dressing change and recorded as a percentage of exposed wound tissue.

On day 2, mean wound debridement for 7,500 ABC units/gram was 78.5%, 3,750 ABC units/gram was 81%, 750 ABC units/gram was 20.5%. Collagenase Santyl ® Ointment was 22.5% and the petroleum jelly (control) was 1.2%. There were statistically significant differences between treatment with 3,750 units/gram as compared to treatment with petroleum jelly control, Santyl ® or 750 units/gram ($P = <0.05$). Two Tailed T Test. There was no significant difference between treatment with 7,500 units/gram and 3,750 units/gram.

On day 3 mean wound debridement for 7,500 ABC units/gram was 92%, 3,750 ABC units/gram was 93%, 750 ABC units/gram was 40.5%, Collagenase Santyl ® Ointment was 49.2% and petroleum jelly control was 6.8%. There were statistically significant differences between treatment with 3,750 ABC units/gram as compared to treatment with petroleum jelly control, Santyl ®, or 750 ABC units/gram ($P = <0.05$) Two Tailed T Test. There was no significant difference between treatment with 7,500 units/gram and 3,750 units/gram.

Mean time to complete wound debridement was: 7,500 ABC units/gram—9.5 days, 3,750 ABC units/gram—9.25 days, 750 ABC units/gram—12.5 days. Collagenase Santyl ® Ointment—12.25 days, and Petroleum Jelly Control—15 days. The difference between treatment with 3,750 ABC units/gram and petroleum jelly control were significant ($P = <0.05$) Two Tailed T Test. The differences between treatment with 3,750 units/gram as compared to treatment with 750 units/gram or Collagenase Santyl ® Ointment were not significant at the 0.05 significance level but would be if a significance level of 0.10 were chosen.

RE-EPITHELIALIZATION

Wounds were considered to be healed after a new layer of epithelium had formed which completely covered the burn site. The investigator estimated the percentage of re-epithelialized tissue daily.

Mean time to 50% re-epithelialization was: 7,500 ABC units/gram—13.8 days, 3,750 ABC units/gram—14.3 days, 750 ABC units/gram—15.47 days, Collagenase Santyl ® Ointment—15.75 days, petroleum jelly control—16.5 days. There were statistically significant differences between treatment with 3,750

ABC units/gram as compared to treatment with petroleum jelly control, Collagenase Santyl ® Ointment, and 750 ABC units/gram. (P= <0.05) Two Tailed T Test. There were no statistically significant differences between treatment with 3,750 ABC units/gram and 7,500 ABC units/gram.

Mean time to 100% re-epithelialization was: 7,500 ABC units/gram—20.75 days, 3,750 ABC units/gram—21 days, 750 ABC units—23 days, Collagenase Santyl ® Ointment—23.5 days, and petroleum jelly control—23.75 days. There were statistically significant differences between treatment with petroleum jelly control, Collagenase Santyl ® Ointment, and 750 ABC units/gram. (P= <0.05) Two Tailed T Test. There were no statistically significant differences between treatment with 3,750 ABC units/gram and 7,500 ABC units/gram.

SAFETY

One animal died on day four of the study and the death is attributed to wrapping the dressings too tightly over the abdomen with nonelastic occlusive tape. Other side effects attributed to wrapping the dressings too tightly were diarrhea, and rectal prolapse.

There were no statistically significant differences between the various treatment groups in the frequency of inflamed and edematous burn fields observed post-treatment.

No side effects such as excessive bleeding of the wound, damage to surrounding viable tissue, or cellulitis were observed during the study.

Due to difficulties encountered by the pathological laboratory in preparing the biopsy tissue, it was not possible to draw any meaningful conclusions from the histopathology specimens.

Evaluation of the hematology and clinical chemistry results yielded no evidence of dose relationships in any of the findings. Those changes which occurred were randomly spread to a few occasional elevations and depressions of a minor nature. The data were reflective of the fact that the collagenase preparations tested were without effect on hematology and clinical chemistry.

CONCLUSIONS

Collagenase in lactose monohydrate NF at a dosage of 3,750 ABC units was clinically and statistically superior to petroleum jelly control, Santyl ® Collagenase Ointment and collagenase in lactose monohydrate NF at 750 ABC units/g in the efficacy parameters of wound debridement and re-epithelialization. There were no significant differences between treatment with 3,750 ABC units/g and 7,500 ABC units/g.

One animal died during the study and this death was attributed to wrapping the dressing too tightly over the abdomen. No serious adverse reactions or side effects attributed to the test articles were observed during the study.

EXAMPLES WITH DEXTRAN

Comparisons were made of the rate of debridement of burns when treated with dextran/collagenase combinations and with collagenase-containing ointment (Santyl ® Ointment; contains 250 ABC units of collagenase per gram of white petrolatum USP; manufactured by Advance Biofactures Corp. of Lynbrook, N.Y. 11563).

Four burn experiments, comprising a total of eighteen guinea pigs, were carried out to compare the debriding effect of dextran/collagenase combinations to that of Santyl ® Ointment. An antibiotic was used in all cases. Thirteen sides were each treated with 3 grams of Santyl ® Ointment. Seven sides were treated with a dextran/collagenase mixture. Sterile gauze pads with a thin layer of sterile petrolatum to avoid sticking were used on all surfaces containing the dextran/collagenase application. 0.5 gm of the dextran/collagenase combination is one application on a burn surface.

Experiment Number I

Neosporin powder was used as the antibiotic in conjunction with Santyl ® Ointment. The powder was first sprinkled on the surface of the wound. Gentamycin cream was used as the antibiotic in conjunction with dextran containing 750 ABC units of collagenase powder per gram of dextran. The dextran/collagenase combination showed faster debridement in the first 48 hours of the experiment. By the fourth day, all sides showed equal percentage debridement. The edge of the burn area was more completely debrided when using the dextran/collagenase powder combination.

Experiment Number II

Santyl ® Ointment containing 0.1% Gentamycin sulfate powder was compared to dextran/collagenase/Gentamycin sulfate powder at 750 ABC units/g and 375 ABC units/g concentrations of collagenase powder in the dextran. The powder contained 0.1% Gentamycin sulfate. The dextran/collagenase/Gentamycin powder with 750 ABC units/g concentration of collagenase showed faster debridement than the other two test preparations in the first 48 hours. By the fourth day, all sides showed equal percentage debridement. The edge of the burn area was more completely debrided when using the dextran/collagenase combinations.

Experiment Number III

This was the same as Experiment Number II, except that an additional two animal sides were treated with a dextran/collagenase/Gentamycin combination containing 1,500 ABC units/g concentration of collagenase. The results showed that the dextran/collagenase combination using all three different concentrations of collagenase exhibited faster debridement in the first 48 hours, with the 1,500 ABC units/g concentration being the fastest compared to Santyl ® Ointment.

Experiment Number IV

The debriding effect of Santyl ® Ointment was compared to that of a dextran/collagenase combination with 1,500 ABC units of collagenase powder per gram of dextran. The antibiotic used was silver sulfadiazine powder sprinkled onto the wound surface before the application of the treatment. At the end of the experiment (4 days), the dextran/collagenase treated side had a greater percentage of debridement than the Santyl ® Ointment treated side.

What is claimed is:

1. A pharmaceutical composition comprising a dry powdered intimate physical admixture of water-soluble dextran and from about 100 to about 10,000 ABC units of collagenase per gram of dextran, said collagenase not being bound to the dextran by an added chemical binding agent.

2. A composition according to claim 1 containing from about 500 to about 5,000 ABC units of collagenase per gram.

3. A composition according to claim 2 containing from about 750 to about 3,000 ABC units per gram.

4. A composition according to claim 1 also containing an antibiotic.

5. A pharmaceutical composition comprising a dry powdered intimate physical admixture of water-soluble dextran and from about 0.01 to about 30 weight percent of a pharmaceutical suited for topical application, said pharmaceutical not being bound to the dextran by an added chemical binding agent.

6. A composition according to claim 5, wherein said pharmaceutical is an enzyme.

7. A composition according to claim 5, wherein said pharmaceutical is an antibiotic.

8. A composition according to claim 7, wherein said antibiotic is gentamycin or a mixture of neomycin sulfate zincbacitracin. and polymyicin B-sulfate.

9. A composition according to claim 5, wherein said pharmaceutical is an anesthetic.

10. A composition according to claim 9 wherein said anesthetic is benzocaine or lidocaine.

11. A composition according to claim 5 wherein said pharmaceutical is an antifungal agent.

12. A composition according to claim 5 wherein said pharmaceutical is an anti-inflammatory agent.

13. A composition according to claim 12, wherein said anti-inflammatory agent is hydrocortisone.

14. A pharmaceutical composition consisting essentially of a dry powdered intimate physical admixture of water-soluble dextran and from about 100 to about 10,000 ABC units of collagenase per gram of dextran.

15. A composition according to claim 14 containing from about 500 to about 5,000 ABC units of collagenase per gram.

16. A composition according to claim 14 also containing an antibiotic.

17. A pharmaceutical composition consisting essentially of a dry powdered intimate physical admixture of water-soluble dextran and from about 0.01 to about 30 weight percent of a pharmaceutical suited for topical application.

18. A composition according to claim 17, wherein said pharmaceutical is an enzyme.

19. A composition according to claim 17, wherein said pharmaceutical is an antibiotic.

20. A composition according to claim 17, wherein said pharmaceutical is an anesthetic.

* * * * *